United States Patent [19]

Bares

[11] 3,999,119
[45] Dec. 21, 1976

[54] MEASURING TONER CONCENTRATION
[75] Inventor: Jan Bares, Webster, N.Y.
[73] Assignee: Xerox Corporation, Stamford, Conn.
[22] Filed: Mar. 26, 1975
[21] Appl. No.: 562,296
[52] U.S. Cl. .............................. 324/32; 118/646; 355/3 R
[51] Int. Cl.² ...................................... G01R 29/12
[58] Field of Search .......... 324/32; 355/3; 118/637; 73/71.2, 70.2, 71.4, DIG. 1; 137/88, 101.19; 259/163; 340/384 E

[56] References Cited
UNITED STATES PATENTS

| 3,376,853 | 4/1968 | Weiler et al. | 118/637 |
|---|---|---|---|
| 3,544,889 | 12/1970 | Alauzet et al. | 324/32 |
| 3,707,134 | 12/1972 | Gawron | 118/7 |
| 3,893,408 | 7/1975 | Lamel | 118/7 |

OTHER PUBLICATIONS
Procedure For Making Triboelectric Measurements, E. C. Giaimo, Jr., RCA Engineer–Engineering & Research Notes, June–July 1971, V17, No. 1, pp. 102–103.

Primary Examiner—Gerard R. Strecker
Assistant Examiner—Vincent J. Sunderdick
Attorney, Agent, or Firm—James J. Ralabate; James H. Laughlin

[57] ABSTRACT

Toner concentration of an electrostatic developer is measured by disposing the developer between two electrodes and agitating the developer to produce electronic noise as a result of triboelectrification and measuring and determining from the generated noise the concentration of the developer.

14 Claims, 10 Drawing Figures

MEASURING TONER CONCENTRATION

BACKGROUND OF THE INVENTION

This invention relates generally to electrophotography and in particular to a method and apparatus for measuring the effective concentration of electrostatic toner powder mixed with a carrier medium. More specifically, the invention relates to method and apparatus, whereby the ability of a xerographic carrier developing material to develop a xerographically formed electrostatic latent image with an optimum image density can be determined.

More particularly, the invention relates to a method and apparatus for determining the concentration of toner particles in a particulate developer mix comprising a triboelectric mixture of electroscopic toner particles and carrier particles. The apparatus of the present invention is particularly useful in electrostatic printing systems wherein electrostatic charge patterns are rendered visible by the application thereto of a particulate triboelectric developer mix of pigmented toner particles and carrier particles.

In order to develop an electrostatic latent image, it is required to dust the image with a developer powder, whereby the powder particles are selectively attracted to the charged areas to form a visible powder particle image of the electrostatic latent image. Development of the image is effected with developers which comprise in general, a mixture of a suitable pigmented or dyed electrostatic powder, hereinafter referred to as "toner" and a granulated carrier material termed "carrier" which by means of cascading over the image functions to carry and to generate triboelectric charges on the toner. These materials are conventional and well known.

The general process of development to which this invention relates is termed "carrier development" but may also be used with other developing systems such as magnetic brush development systems. In general, in carrier development the toner composition is loosely coated on the carrier surface to which it remains loosely affixed by reason of electrostatic attraction thereto. The type of carrier development most widely used commercially is called "granular" or "cascade" carrier development. This system is more fully described in U.S. Pat. No. 2,618,551 to L.E. Walkup and U.S. Pat. No. 2,638,416 to Walkup and Wise. In this process the electroscopic toner is desirable mixed with a granular carrier, either electrically conducting or insulating, magnetic or non-magnetic, provided that the particles of granular material when brought in close contact with the toner particles acquire a charge having an opposite polarity to that of the granular carrier particles and adhere to and surround the granular carrier particles.

In this development process, only the toner particles are consumed and the carrier particles remain and are constantly reused. Consequently, it is necessary to replenish the developer mix with additional toner particles periodically or continuously to maintain the concentration of toner particles in the developer mix within predetermined limits and to insure developed prints of proper density. If, for example, the concentration of toner particles in the developer mix is less than an optimum concentration, the density of the developer charge pattern is too light. On the other hand, if the concentration of the toner particles in the developer mix is too high, the excessive toner particles tend to adhere to the non-image areas of the print, providing prints with a "dirty," grayish background.

It has been proposed to monitor the concentration of toner particles in the developer mix by photoelectric methods, such as by measuring the light reflected from samples of developer mix, or by measuring the light from developed electrostatic charge patterns, but such apparatus is relatively complex, requires delicate adjustments, and is affected by external conditions, such as dust, the color of the pigment toner, and the color of the recording element involved.

Other measuring systems take into consideration variations in magnetic permeability, dielectric permittivity, electrical conductivity or combinations of these to indicate variations in the ratio of carrier to toner. For example, as described in U.S. Pat. No. 3,802,381 an externally applied electric or magnetic field is established in the area of a quantity of developer mix consisting of a toner and a carrier and a measurement of one or more of the aforementioned parameters is employed to indicate the need for a greater or lesser percentage of toner or carrier in the developer. The apparatus for indicating the carrier/toner ratio includes provisions for establishing an electric or magnetic field in a quantity of mix and provisions for providing an output signal representative of one or more of these parameters exhibited by the developer mix. Thus, this toner concentration detection technique utilizes the toner carrier mixture as a passive circuit element.

In addition, some of the known toner concentration control systems have the deficiency that when the developer tribo is very low due to developer material fatigue (degradation) for example, or after a prolonged period during which the copier was not used, as over a weekend; detect this as low toner concentration and further damage the quality of prints by increasing an already normal toner concentration above the acceptable level.

SUMMARY OF THE INVENTION

Briefly stated, and in accordance with the present invention the concentration of toner in a developer is measured by disposing the developer between two electrodes and agitating the developer to produce electronic noise as a result of triboelectrification and measuring and determining from the generated noise the concentration of toner in the developer. It is not necessary to provide external electrical power to the developer as required by the prior art. In other words, in the prior art the developer constitutes a passive element in the control scheme, while in the present invention the agitated developer is a source of a measurable electrical signal.

The apparatus for determining the toner concentration may comprise parallel spaced electrodes between which may or may not be provided means for containing the developer mix and means for sufficiently agitating the developer to produce detectable electronic noise and means for measuring the intensity of the electronic noise generated.

When the normal flow of developer in the developing operation results in sufficient agitation of the developer within the electrostatic copier, the apparatus for determining toner concentration may be mounted on the interior surface wall of the developing housing thereby eliminating the need to provide external agitation since the internal flow of the developer produces sufficient agitation to generate sufficient electronic noise which can be detected and measured to determine the toner concentration of the developer within the electrostatic copier.

When the amount of agitation or normal flow of the developer in the electrostatic copier is insufficient to generate sufficient detectable noise, means are provided for sufficiently agitating the spaced electrodes within the electrostatic copier to provide sufficient agitation to generate detectable noise which represents the toner concentration.

DESCRIPTION OF THE PREFERRED EMBODIMENTS

It has been determined that electronic noise is generated when a developer comprising a toner and a carrier is agitated between spaced electrodes. It has also been observed that the intensity of this electronic noise decreases with increased toner concentration and increases with the specific charge of the toner. This forms the basis of the present invention.

When a weighed amount of carrier or carrier/toner mixture is placed in a polystyrene Petri dish and electrodes attached to the top and bottom of the dish and connected to electronic noise detecting means (such as a differential amplifier) and frequency analyzer and shaken in a laboratory shaker, the system produces electronic noise, the intensity of which decreases with increasing toner concentration. This can be seen by reference to FIGS. 9 and 10 which show the noise detected at various concentrations of toner.

One explanation, based on available date of this effect shows that the noise consists of two components: (a) the predominantly low frequency noise caused by moving charged carrier beads, and (b) the higher frequency noise due to contact discharges between the carrier beads and between the beads and dish walls, especially bottom. The source of triboelectric charging is obviously bead-dish wall interface. Toner which adheres to the carrier reduces the surface available for triboelectrification and consequently the measured noise voltage. While it is believed that this description accurately describes the theory of the invention, the invention is not restricted to this theory of operation.

Figure 1:
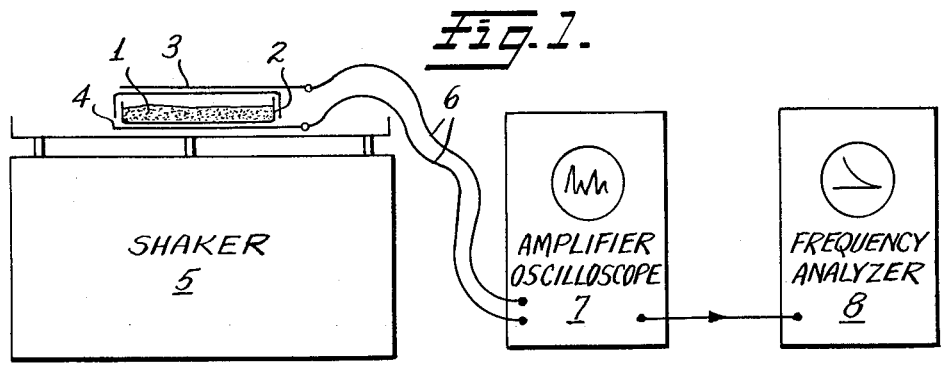
FIG. 1 is a diagrammatic view of parallel spaced electrodes containing developer disposed therebetween placed on a shaker with the electrodes being connected to an amplifier oscilloscope and frequency analyzer.

The noise produced can generally be detected in a wide band starting from above power line frequency or above the frequency of any other disturbing signal or copier vibration. Specifically, it can be detected in the band 500 Hz – 500 k Hz or, in a 1 k Hz – 10 k Hz band, as well. The electronic circuits used to measure the noise intensity may consist of an oscilloscope and a frequency analyzer as shown in FIG. 1; a tuned AC millivolt meter, a RMS millivolt meter with a band-pass filter or the like. When either a tuned AC millivolt meter or a RMS millivolt meter with a band-pass filter is used, the RMS signal may be smoothed electronically if desired.

In addition, when automatic control of toner concentration is desired the signal from the electrodes may activate known mechanisms for supplying measured additional toner to the developer chamber. Also, when automatic control of toner concentration is desired and to prevent occassional electrical disturbance or transients exceeding the developer noise level from activating the toner replenisher, the RMS noise voltage should be further electronically smoothed by a time averaging circuit. Examples include circuits with high time constant, integration of the RMS noise signal over predetermined time intervals with the subsequent reset to zero, or other techniques well known to those skilled in electronics and control systems design.

The above described principle forms the basis for determining the toner concentration in an electrostatic developer containing carrier particles and toner particles. The method of this invention is based upon this discovery and comprises disposing a developer between two electrodes and agitating the developer to produce electronic noise generated as a result of triboelectrification and measuring this generated noise to determine the concentration of toner present.

One form of the invention is seen in FIG. 1 wherein a weighed amount of carrier or carrier/toner material 1 is placed in a polystyrene Petri dish 2, a top electrode 3 and a bottom electrode 4 are attached to the top and bottom of the dish respectively. The electrodes are connected via conventional conductors 6 to a differential amplifier and oscilloscope 7 and a frequency analyzer 8. When the Petri dish 2 is shaken by a conventional shaker 5, the system produces electronic noise the intensity of which is decreased with increasing toner concentration. It has been discovered empirically that the intensity of electronic noise in an agitated developer decreased with increased toner concentration.

Thus, it can be appreciated that the detected electronic noise can be empirically determined for any developer systems at various toner-carrier concentrations and once these values are determined the toner concentration of a given system can be determined simply by measuring the noise generated and correlating the amount of noise to the toner concentration for the given system. Of course, this may be done directly by calibrating the noise detecting instrument in terms of toner concentration.

In addition, it has been found that the majority of the noise signal is delivered by the bottom electrode. Accordingly, the shaker Petri dish setup can be replaced by an insulated or uninsulated electrode (probe) with an adequately large surface immersed in the developer. The RMS voltage of the noise signal recovered from the probe electrode can be interpreted in terms of toner concentration. Since there are no specific requirements for the electrode or probe size, the dimensions of the probe and its place in the developer housing is chosen according to the size and shape of the developer housing which contains the developing mixture as shown in FIGS. 3–8. However, it is preferable for the high voltage or pickup electrode to have a surface area of at least 1 to 2 square inches. In FIGS. 6 and 8, the high voltage electrodes are designated 54 and 61 respectively while the low voltage or grounded electrode encloses the high voltage or pickup electrode in order to reduce pickup of outside disturbances. The grounded electrode thus shields the pickup electrode and a portion of the sample developer.

One embodiment of the present invention consists of a small and easy-to-carry device which can be used in the field. This device will enable one to check easily and quickly the triboelectric charging of a developer. The toner concentration may be determined after the maximum charging level of the developer has been reached.

Figure 2:
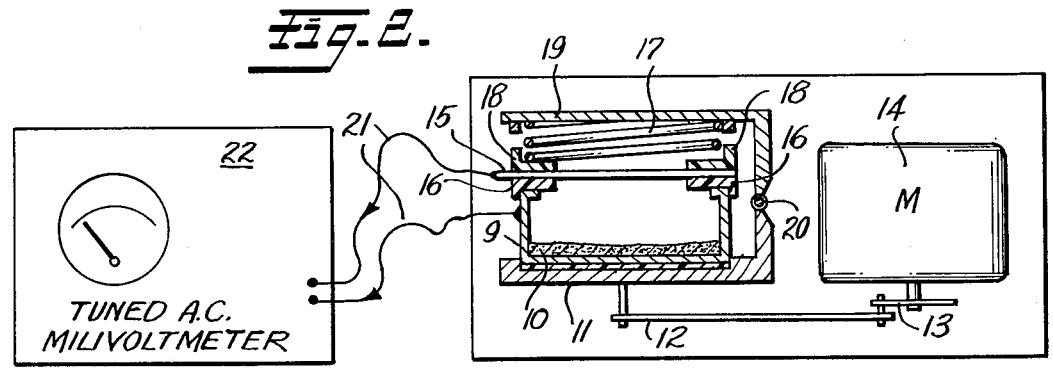
FIG. 2 is a diagramatic view of a field type measuring device which includes a tuned AC millivolt meter connected to an upper electrode and a lower dish electrode containing the developer mix connected to a motor for providing agitation.

Such a field type measurement device is illustrated in FIG. 2 wherein a stainless steel dish electrode 9 containing developer 10 is placed on base member 11 connected via a conventional linkage mechanism 12 to an eccentric drive 13 on a motor 14 thereby providing the necessary vibration to cause agitation of the developer. Of course, any kind of mechanical arrangement may be utilized which provides the necessary agitation to the developer including any kind of periodic motion like rocking or the like and may even include rotation depending upon the particular construction of the driving mechanism. The stainless steel dish 9 forms one electrode in this embodiment, however, a separate electrode may be used instead. A second upper electrode 15 is placed over the dish 9 and is insulated therefrom by dielectric washers 16.

Electrode 15 is exposed to the developer although the vibrating motion is not sufficient to cause contact between the developer and electrode 15. However, even if such contact is obtained, the results are the same, that is detectable noise is produced which may be correlated to provide toner concentration. A spring 17 biases the upper electrode 15 against the lower electrode dish 9. The spring is insulated from the upper electrode by dielectric washers 18. An upper member 19 pivoted to member 11 at 20 serves as the necessary support for bias spring 17. Thus, a capacitor is formed by upper electrode 15 and dish 9. These electrodes 9 and 15 are connected via conductors 21 to a band-pass filter tuned AC millivolt meter 22.

In this specific embodiment the stainless steel dish forms dish electrode 9 and a flat aluminum plate forms upper electrode 15. However, the two electrodes may be made of the same conducting materials. In fact, all that is required is that the electrodes be made of conducting materials which may include metals and nonmetals such as graphite. Also, the shape and size of the electrodes is not limited provided that sufficient space is provided there between for the agitated developer. For example, one electrode may be dish like in shape to actually contain the toner with the second having a flat sheet-like shape to act as a lid as shown in FIG. 2. Alternatively, the shape of the second electrode may be circular or the like. It may also be a pickup wire. Thus, one electrode may comprise a flat elongated cylindrical container open at one end for receiving the toner and closed on the other to contain the toner therein or the two electrodes may simply form a parallel plate capacitor. The system using metal electrodes in contact with developer mix as shown, for example, in FIG. 2 is preferred over a system where the electrodes are insulated from the developer mix as shown, for example, in FIG. 1.

Figure 3:
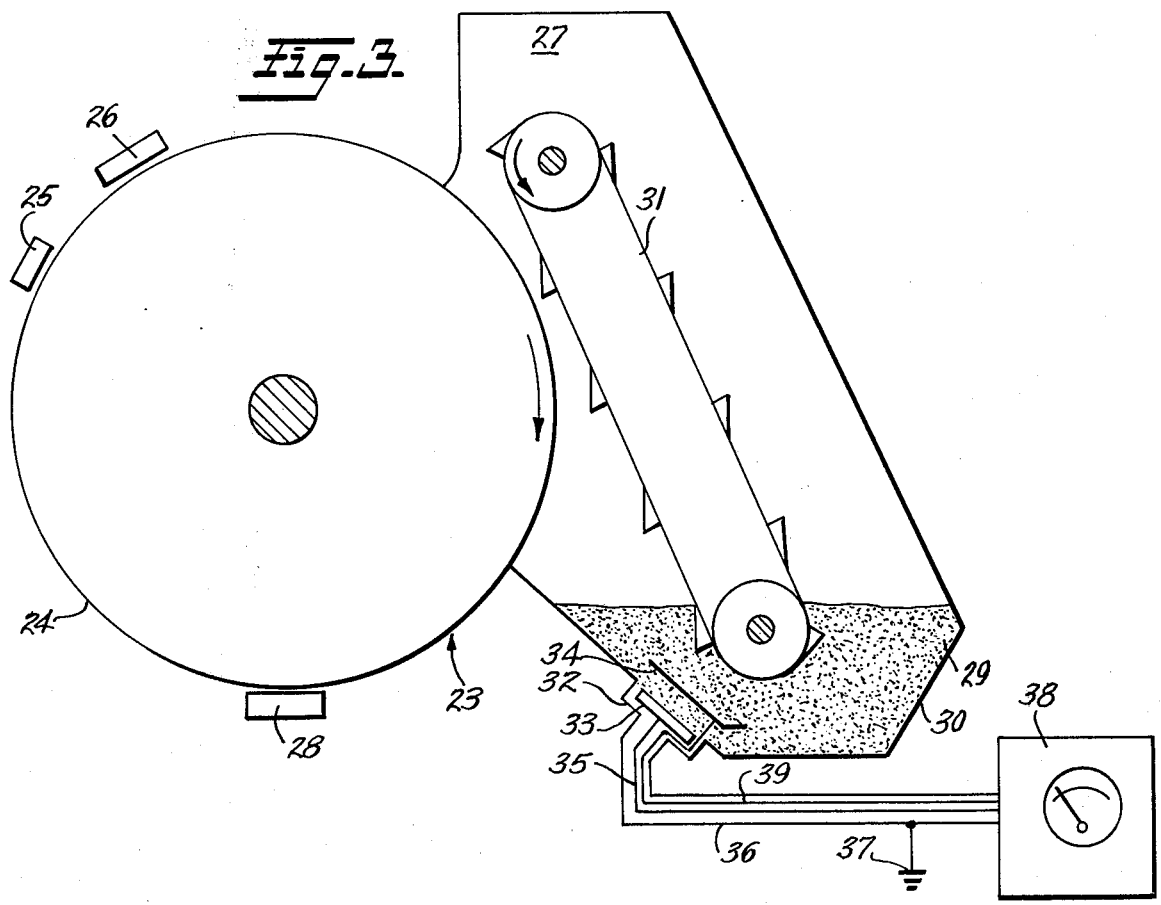
FIG. 3 is a diagramatic view of an electrostatic printing apparatus, and shows stationary electrodes mounted within the developer housing of the printing apparatus.

Referring now to FIG. 3, there is illustrated a xerographic apparatus 23 which may, for example, be of a type disclosed in Crumrine et al, U.S. Pat. No. 2,852,651 in which a xerographic plate in the form of a rotating drum 24 is charged by conventional charging apparatus 25 and then exposed by an exposure means 26 to an image of activating radiation to form an electrostatic latent image on the drum surface to be developed. Development is effected by developing apparatus 27 after which the developed image may be utilized by a utilization apparatus 28.

As illustrated, there is shown a developing mixture 29 in a sump area 30, the developer is conveyed via a rotating conveyor means 31 onto the drum 24 in a conventional manner. The apparatus described to this point is conventional.

A stationary probe 32 having electrode 33 and a shield electrode 34 is positioned adjacent to the base of the sump 30 and is exposed to the developing material 29 as a result of the movement of rotating conveyor means 31. A coaxial lead having an interior conductor 35 and an exterior conductor 36 which is grounded at 37 connects the stationary probe 32 to a conventional tuned AC millivolt meter 38. Shielding electrode 34 is connected to the millivolt meter by conductor 39.

Figure 4:
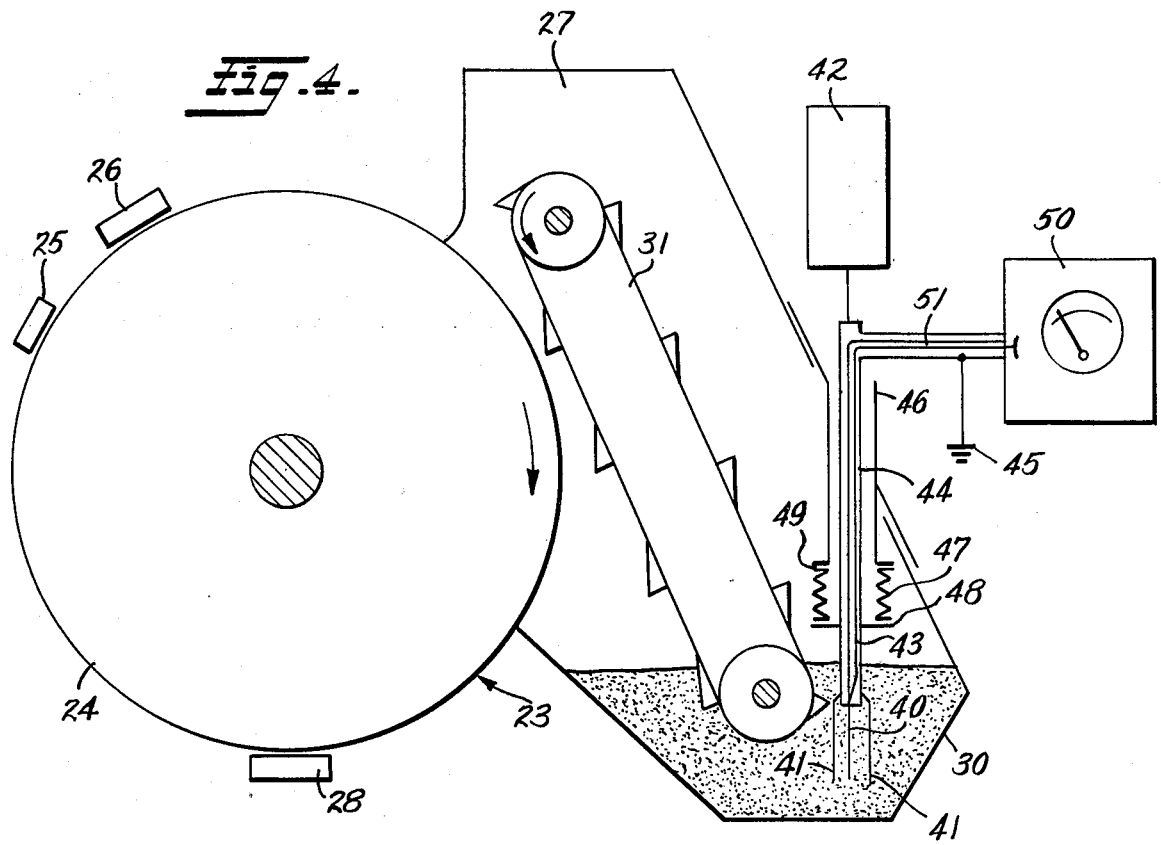
FIG. 4 is a diagramatic view of an electrostatic printing apparatus, and shows vibrating electrodes mounted within the developer housing of the printing apparatus.

FIG. 4 represents a similar type xerographic apparatus as shown in FIG. 3 with a vibrating probe electrode 40 and shield electrodes 41 which are insulated from electrode 40 and form a rigid configuration with electrode 40 so as to allow the combination of electrodes to move as a unit. These electrodes are connected to an electromagnet or an electromotor drive 42, and probe electrode 40 is connected to an internal conductor 43 of a coaxial cable having an external conductor 44 which is grounded at 45. A suitable housing or casing means 46 surrounds the vibrating probe and has a rubber bellows 47 connected to the probe by annular member 48 and to the housing at 59. The bellows arrangement 47 and housing 46 serve to prevent the developer mixture from adhering to the upper portions of the probe and from being exposed to the external atmosphere and environment. Probe electrode 40 is connected to a conventional tuned AC millivolt meter 50 by conductor 43 and shield electrode 41 is connected to the millivolt meter by conductor 51. By means of this apparatus, it is possible to measure the toner concentration in the sump of an electrostatic developer in which the movement of the developer in the conventional developing process does not provide sufficient agitation.

Figure 5:
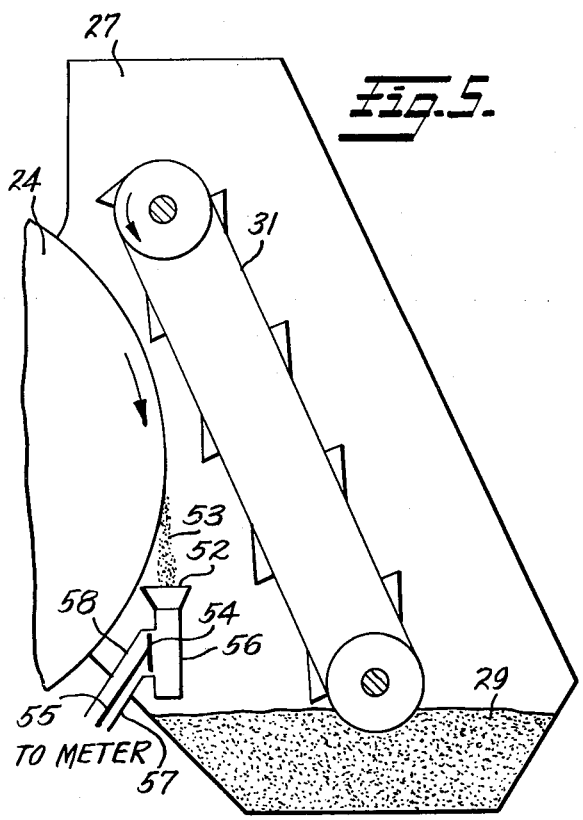
FIG. 5 is a diagramatic view of an electrostatic printing apparatus and shows a funnel type electrode mounted within the housing and in the path of falling toner particles.
Figure 6:
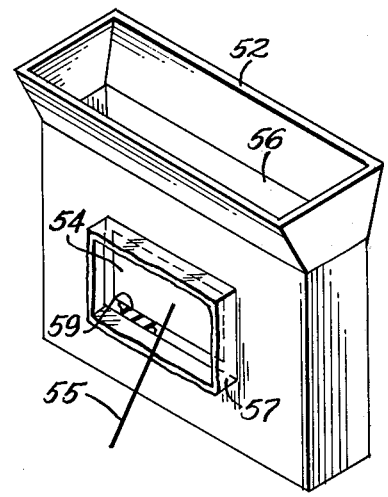
FIG. 6 provides a more detailed view of the funnel type electrode.

FIG. 5 shows the placement of funnel like probe 52 so positioned in the conventional developing apparatus so that falling developer 53 which is not used in forming the image passes therethrough before being returned to the sump. While it is necessary to use measured amounts of developer mix when a dish like electrode arrangement is used, constant amounts of developer mix between the electrodes is insured by use of funnel shaped electrodes to secure a constant supply of developer mix over some averaging interval of time. This may also be accomplished by immersion of the electrodes into the developer mix. The electrodes should therefore be arranged so that the amount of developer (or its flow) is constant when averaged over a reasonably long time interval still acceptable for the proper toner concentration control performance.

Funnel like probe 52 consists of electrode 54 which is insulatedly mounted in the wall of the funnel like probe and connected via a conductor 55 to a tuned AC volt meter (not shown). Insulated electrode 54 and the opposite wall 56 of the funnel form a capacitor. Opposite wall 56 is attached by a conductor 57 to the volt meter (not shown). Probe 52 is attached to the interior wall of developing apparatus by housing 58.

A more detailed view of funnel like probe 52 is shown in FIG. 6. As can be seen in FIG. 6 electrode 54 is insulated from the remaining portion of the funnel like probe by dielectric material 59. Thus, electrode 54 and the opposite wall of the funnel 56, form a capacitor. Funnel walls also shield the electrode and prevent it from picking up disturbing signals. Of course, the funnel electrode may be vibrated if additional agitation of the developer is necessary.

Figure 7:
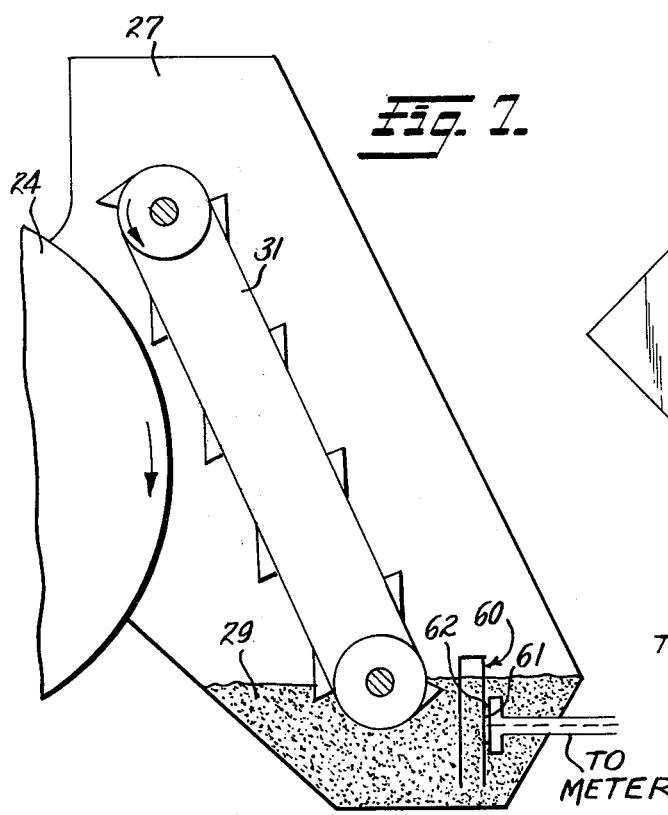
FIG. 7 is a diagramatic view of an electrostatic printing apparatus and shows a parallel spaced electrode mounted within a developer sump.
Figure 8:
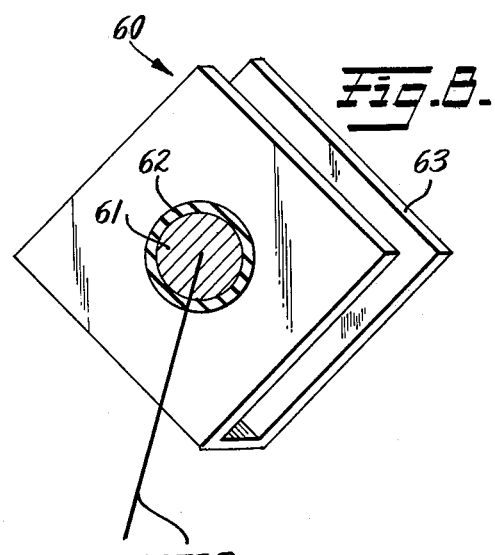
FIG. 8 is a top planar view of the parallel spaced electrode.

FIG. 7 shows a still further embodiment of the invention which shows probe 60 positioned in the developer sump. Of course, probe 60 may be vibrated in any direction including also motions perpendicular to the plane of the drawing if necessary.

FIG. 8 shows a more detailed view of a portion of probe 60 which shows electrode 61 separated from the remaining portion by dielectric material 62. Side 63 and electrode 61 form a parallel plate condenser. Though the pickup electrode 61 is shielded, the developer may still pass along its surface. Probe 60 has a U-shape configuration as shown.

Although the various electrode arrangements have been described with respect to a cascade type developing system the toner concentration in other conventional developing systems may also be monitored using the method and apparatus described. The arrangement of electrodes shown in FIGS. 3 to 8 may similarly be positioned in a magnetic brush development system. For example, the funnel of FIG. 5 may be placed in such a way that the developer mixture, i.e. toner and carrier, falling off the magnetic brush will be collected in the funnel, alternatively, the pickup probe electrode can be positioned directly against the drum in the magnetic brush developing apparatus.

Figure 9:
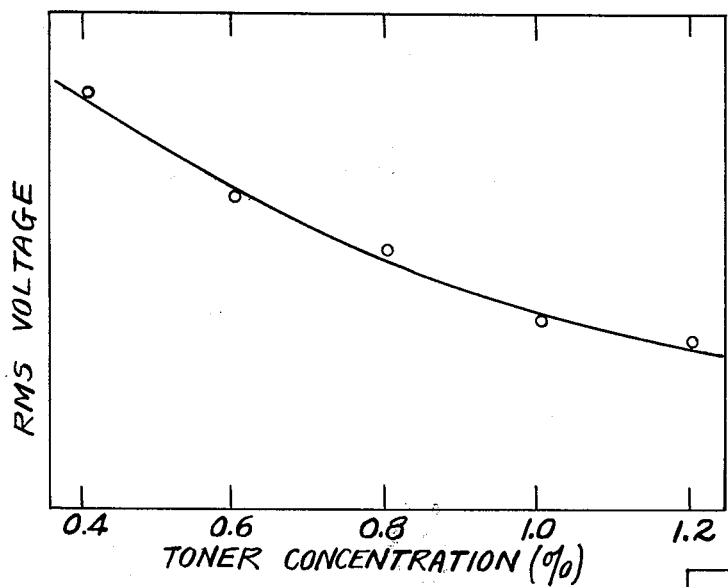
FIGS. 9 and 10 show the dependency of electronic noise on toner concentration.

FIG. 9 is a graph of the detectable noise measured using the apparatus of FIG. 1. That is, the disposable polystyrene Petri dish with a measured amount of developer is placed in the capacitor formed by parallel spaced electrodes 3 and 4 of FIG. 1. The capacitor is directly connected to the electric motor providing shaking motion. The noise RMS voltage is read instantly and a calibration curve can be provided for each developer type or the meter can be calibrated directly in toner concentration. The high pass filter limit was 10 k Hz.

Using this arrangement and 4 inch polystyrene Petri dishes, 10 gms. of MTP (methylterpolymer) coated steel carrier 250$\mu$ in diameter and 364 toner samples having varying toner concentrations were shaken at a tumbling velocity of about 180c/min. As can be seen from FIG. 9, the RMS voltage decreases for toner concentration ranging from less than 0.4% to more than 1.2%.

Figure 10:
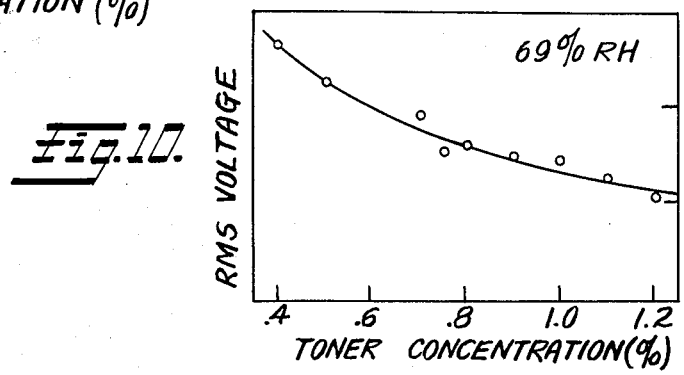

FIG. 10 shows the RMS noise voltage versus toner concentration relationship for the experimental arrangement shown in FIG. 2, wherein a stainless steel dish is used. Again, MTP coated steel carrier was used having a diameter of 250$\mu$ and 364 toner. The samples had the various concentrations as indicated in the figure. The developer mix was shaken to provide a tumbling velocity of about 180c/min., the high pass filter limit was 1 k Hz and the amplifier gain 0.5mV/cm. The relative humidity was 69% and the results vary only slightly with relative humidity.

What is claimed is:

1. A method for determining toner concentration in an electrostatographic developer containing carrier particles and toner particles which comprises disposing an electrostatographic developer comprising toner particles and carrier particles between two electrodes, agitating the developer to produce electronic noise generated as a result of triboelectrification, and measuring said generated noise to determine the concentration of toner present.

2. The method of claim 1 whereby the developer is agitated by means of the flow of the developer in an electrostatic copier.

3. The method of claim 1 whereby the electrodes are vibrated to effect agitation of said developer.

4. The method of claim 1 whereby a band-pass filter and an AC millivolt meter is used to measure said generated noise.

5. The method of claim 1 whereby the toner concentration is continuously measured.

6. The method of claim 1 whereby the said electrodes form a parallel plate capacitor.

7. An apparatus for determining toner concentration of an electrostatographic developer which comprises parallel spaced electrodes, means for containing an electrostatic developer comprising toner and carrier particles between said electrodes, means for agitating said developer sufficiently to generate electronic noise as a result of triboelectrification, and means for detecting and measuring said generated electronic noise and determining said toner concentration.

8. The apparatus of claim 7 whereby means for containing developer comprises a flat elongated cylindrical container, open at one end and closed at the other.

9. An apparatus for continuously monitoring the toner concentration in the developer of an electrostatographic copier which comprises a grounded electrode, means for vibrating said electrode, and means for detecting and measuring generated electronic noise as a result of triboelectrification, said noise created by agitation of the developer by said vibrating electrode.

10. The apparatus of claim 9 whereby said vibrating means comprises a bellows and solenoid.

11. The apparatus of claim 9 whereby said means for detecting and measuring generated electronic noise is a millivolt meter.

12. An apparatus for continuously monitoring the toner concentration by agitation for generating electronic noise by triboelectrication in an electrostatographic copier which comprises stationary spaced electrodes, means for mounting said electrodes within the sump of an electrostatographic copier, and means for detecting and measuring said generated electronic noise.

13. The apparatus of claim 12 whereby said spaced electrodes form a parallel capacitor.

14. The apparatus of claim 13 whereby said parallel capacitor has a flat funnel shape.

* * * * *